United States Patent [19]

Palmer et al.

[11] Patent Number: 4,476,238
[45] Date of Patent: Oct. 9, 1984

[54] SEPARATION OF TARS FROM CARBONYLATION REACTION MIXTURES

[75] Inventors: Burton J. Palmer, Upper Montclair; Joseph V. Posluszny, Wharton, both of N.J.

[73] Assignee: The Halcon SD Group, Inc., New York, N.Y.

[21] Appl. No.: 267,961

[22] Filed: May 28, 1981

[51] Int. Cl.³ .............. B01J 27/32; B01J 23/96; C07C 51/56; C07C 67/37
[52] U.S. Cl. .................. 502/31; 260/546; 260/549; 502/26; 502/28; 502/29; 502/32; 502/33; 560/232
[58] Field of Search .......... 252/412, 414, 415; 260/549, 546; 562/607, 608, 517; 423/22; 560/232; 502/24, 29-33, 26, 28

[56] References Cited

U.S. PATENT DOCUMENTS

| | | | |
|---|---|---|---|
| 2,839,580 | 6/1958 | Hughes et al. | 260/597 |
| 2,880,241 | 3/1959 | Hughes et al. | 260/604 |
| 3,420,873 | 1/1969 | Olivier | 260/497 |
| 3,539,634 | 11/1970 | Olivier | 260/604 |
| 3,547,964 | 12/1970 | Olivier | 260/429 |
| 3,560,539 | 2/1971 | Booth | 260/429 |
| 3,579,552 | 5/1971 | Craddock et al. | 260/413 |
| 3,641,076 | 2/1972 | Booth | 260/429 R |
| 3,716,626 | 2/1973 | Kniese et al. | 423/418 |
| 3,821,311 | 6/1974 | Hughes et al. | 260/604 HF |
| 3,857,895 | 12/1974 | Booth | 260/604 HF |
| 3,887,489 | 6/1975 | Fannin | 252/413 |
| 3,899,442 | 8/1975 | Friedrich | 252/416 |
| 3,920,449 | 11/1975 | Onoda et al. | 75/97 R |
| 3,978,148 | 8/1976 | Citron | 423/22 |
| 4,013,583 | 3/1977 | Khifton | 252/415 |
| 4,021,463 | 5/1977 | Kummer et al. | 260/429 R |
| 4,340,569 | 7/1982 | Davidson et al. | 423/22 |
| 4,340,570 | 7/1982 | Davidson | 423/22 |
| 4,341,741 | 7/1982 | Davidson | 423/22 |
| 4,364,907 | 12/1982 | Barnes | 423/22 |

FOREIGN PATENT DOCUMENTS

| | | | |
|---|---|---|---|
| 8024 | 7/1979 | European Pat. Off. | |
| 1468940 | 5/1974 | United Kingdom | |
| 1538782 | 2/1976 | United Kingdom | |
| 2054394A | 2/1981 | United Kingdom | 252/411 R |

OTHER PUBLICATIONS

L. R. Snyder, "Classification of the Solvent Properties of Common Liquids", Journal of Chromatography, 92 (1974), 223-230.

Primary Examiner—P. E. Konopka
Attorney, Agent, or Firm—William C. Long; R. T. Stewart; Harold N. Wells

[57] ABSTRACT

Tarry residues often are formed in carbonylation reactions, such as those in which esters or ethers are carbonylated to produce ethylidene diacetate or carboxylic acid anhydrides, such as acetic anhydride. Such residues contain Group VIII noble metal catalysts, typically rhodium, which must be separated before the residues can be disposed of. In the process of the invention, the residues are extracted with solvents which preferentially dissolve the tars. Preferred solvents include alkanes, cycloalkanes, halogenated alkanes, and aromatic hydrocarbons, particularly cyclohexane, carbon tetrachloride, and toluene. Separation of the residues from the noble metal catalyst by solvent extraction makes possible the disposal of the residues and the return of the noble metals to the reaction for reuse.

9 Claims, 1 Drawing Figure

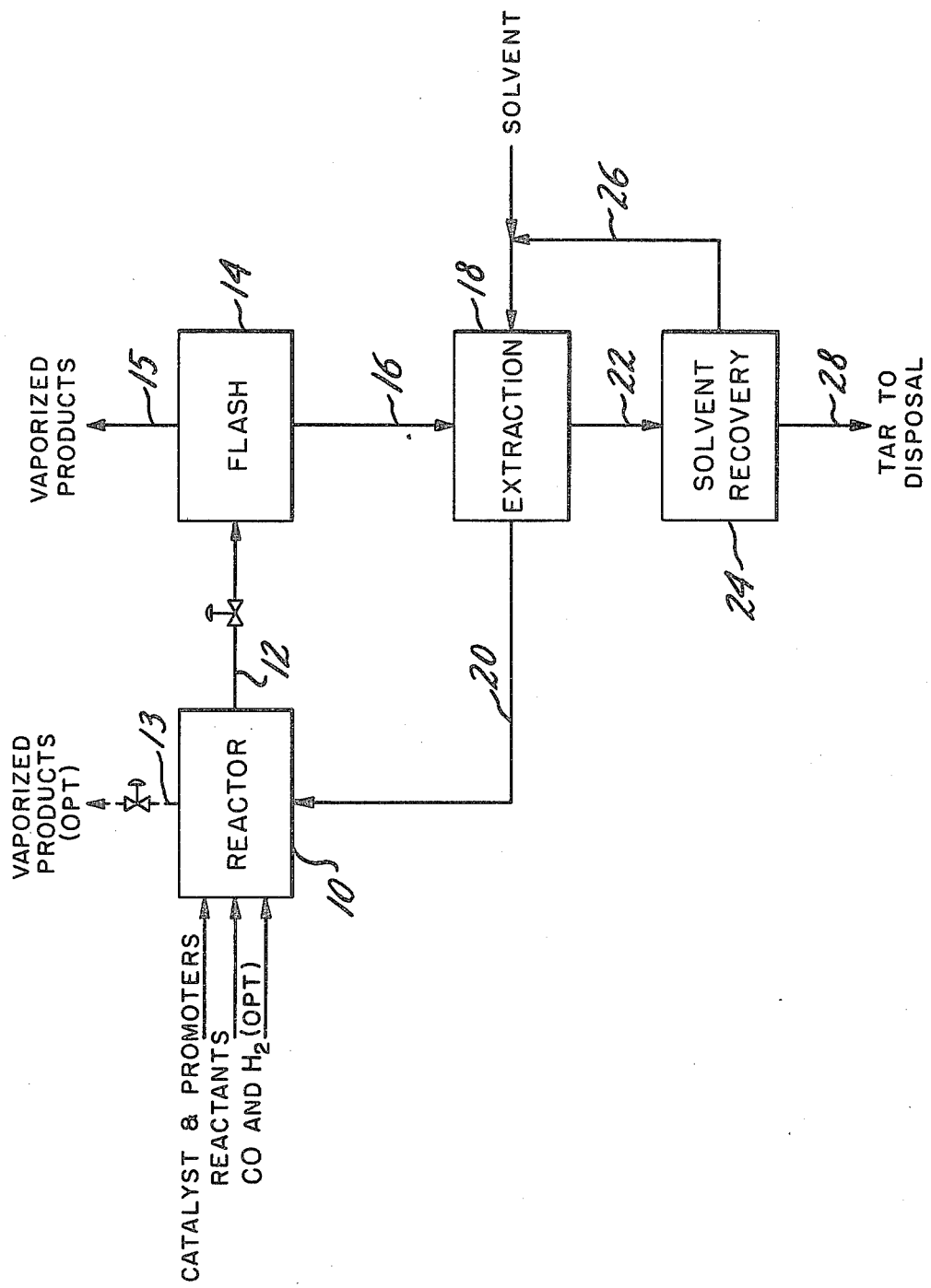

SEPARATION OF TARS FROM CARBONYLATION REACTION MIXTURES

PRIOR ART

Complex catalysts employing Group VIII noble metals, particularly rhodium, are used for the homogenous catalysis of reactions in which carbon monoxide with or without hydrogen may be reacted with various organic molecules to produce compounds having a higher molecular weight. The reactions of particular interest with respect to the present invention are those generally designated as hydroformylation and carbonylation. Such reactions are shown in many patents, for example U.S. Pat. No. 3,579,552 and British Pat. Nos. 1,468,940 and 1,538,782. The noble metal catalysts are considered to be complexes which typically include carbon monoxide, promoting metals, and/or non-metallic promoters.

Reaction products must be separated from the homogenous catalyst. Typically, this is done by distilling the reactor effluent to separate the organic compounds and leaving behind the noble metal catalyst and other heavier materials which can then be recycled to the reaction vessel. The prior art discloses means by which the noble metal is recovered directly from reactor effluents for further use. However, in general the art indicates that heavy residues accumulate and must be purged from the reaction system. Such residues contain substantial amounts of noble metal which must be recovered in order for the process to be carried out economically. Since rhodium is the principal noble metal used, the discussion herein will refer specifically to rhodium, but it is to be understood that other noble metals are not excluded. Palladium alone, or in mixtures with rhodium, is also a particularly useful catalytic metal.

Rhodium has been recovered by many techniques, but at least three general approaches have been disclosed. First, the rhodium is recovered as the metal itself, which could require reformulation of the catalyst for further use. Second, the rhodium may be recovered on a solid material, which may serve as a catalyst support. Third, the rhodium is recovered in a form acceptable for returning to the reactor, with or without some additional processing to improve its catalytic properties.

Rhodium may be recovered as a metal by pyrolysis as shown in U.S. Pat. No. 3,920,449, which involves the high temperature decomposition of residues and rhodium-containing catalyst. The rhodium typically is recovered as the metal or oxide and can then be reprocessed as required to provide catalyst or catalyst precursors for recycle to the reaction mixture.

The second recovery technique may be illustrated by U.S. Pat. No. 3,899,442 in which rhodium is deposited on a solid support in conjunction with pyrolysis of the residues. An alternative is shown in U.S. Pat. No. 3,978,148 in which rhodium is adsorbed on activated carbon, from which it could be recovered.

Rhodium also may be recovered by precipitation from solution in a form which is not necessarily metallic, but may be returned directly to the reaction vessel or pretreated before the recycling. Many methods of this sort have been disclosed in the prior art. Although the catalyst typically is soluble under reaction conditions, it may be possible to form insoluble compounds by the addition of water as shown in U.S. Pat. Nos. 2,839,580, 2,880,241, and 3,821,311. U.S. Pat. No. 3,887,489 shows the precipitation of rhodium-containing compounds by heating reaction residues for a sufficient period of time and temperature. Another technique shown in U.S. Pat. No. 3,560,539 is the use of hydrogen or hydrides to reduce carbonyl content of the tar to hydroxyl groups and thereby to release the rhodium complex which precipitates and can be recovered. The selective adsorption on solids, such as silica, of the residues to separate them from the rhodium catalyst is shown in U.S. Pat. No. 3,539,634. A solvent then is used to recover the residues from the adsorbing solids. The opposite approach, namely, the adsorption of rhodium on a solid adsorbent is disclosed in U.S. Pat. No. 3,716,626.

Rhodium can also be extracted from reaction residues with strong acids accompanied by water and other solvents. Typical disclosures are found in U.S. Pat. Nos. 3,420,873, 3,641,076, and 3,857,895. Related treatments with acids and peroxides are shown in U.S. Pat. Nos. 3,547,964 and 4,021,463.

In connection with the carbonylation process to be completely described both hereinafter and in British Pat. Nos. 1,468,940 and 1,538,782, it has been found that carbonylation reaction residues are not easily separated from the rhodium which they contain. In commonly-assigned patent applications filed Mar. 6, 1981 having Ser. Nos. 241,193, 241,180, and 241,181, the use of amine treatments to assist the extraction of rhodium by acids is disclosed. Now, it has been found that the tars can be preferentially extracted from the reaction mixture with suitable solvents.

SUMMARY OF THE INVENTION

The residues created during carbonylation reactions, particularly the carbonylation of esters or ethers, especially carbonylation of methyl acetate or dimethyl ether to acetic anhydride or ethylidene diacetate, are resistant to the extraction of Group VIII noble metal catalysts, typically rhodium, by strong acids. It has been found that if carbonylation reaction mixtures or concentrates thereof are contacted with suitable solvents, the tars can be preferentially extracted, thereby separating them from the rhodium (or other noble metal). The tars can be separated from the solvent and disposed of and the solvent reused.

Certain solvents have been found to extract some rhodium as well as the tars. Others have been found to extract the tar portions of the residues quite selectively and to leave substantially all of the rhodium behind. Suitable solvents for such preferential extraction of tar are the alkanes, cyclo alkanes, halogenated alkanes, and aromatic hydrocarbons. More generally, the solvents may be characterized as belonging to groups I, VIb, and VII as defined by L. R. Snyder, *J. of Chromatography* 92, 223–230, 1974, plus the alkanes and cycloalkanes which are not assigned to a group by Snyder. In particular, cycloalkanes such as cyclohexane are preferred, along with aromatic hydrocarbons, such as toluene. Other particularly useful classes of solvents are the halogenated alkanes, such as carbon tetrachloride and alkyl ethers. Typically, a volume ratio of about 0.5–10 of solvent to tar is employed.

BRIEF DESCRIPTION OF THE DRAWINGS

The sole FIGURE is a block diagram showing generally how the invention may be applied to a carbonylation reactor.

DESCRIPTION OF THE PREFERRED EMBODIMENTS

The recovery of Group VIII noble metals, especially rhodium, from carbonylation and hydroformylation reaction residues has been of considerable interest to those skilled in the art particular concern to the present inventors is the recovery of Group VIII noble metals, particularly rhodium, from catalysts used in the carbonylation of a carboxylate ester or an alkyl ether to an anhydride, especially the carbonylation of methyl acetate or dimethyl ether to acetic anhydride. In another aspect, the invention relates to recovery of similar rhodium catalysts used for carbonylations in the presence of hydrogen, particularly the carbonylation of methyl acetate and/or dimethyl ether to ethylidene diacetate. These processes have been described in depth in British Pat. Nos. 1,468,940 and 1,538,782 and are summarized below. The processes are important since they produce chemicals of value, both for direct use and as intermediates. However, the recovery of Group VIII noble metals according to the present invention is not considered to be limited to the carbonylation processes of particular interest.

RECOVERY OF NOBLE METALS

The invention broadly relates to the selective removal of tars, i.e. heavy high-boiling residues, produced by carbonylation reactions, with or without hydrogen being present. These heavy residues are complex and their composition is not fully characterized. Where they have been produced during the carbonylation of ester or ethers, they are known to contain high molecular weight compounds with organic carbonyl and acetate functions. If a sample of a carbonylation reaction mixture is flashed and concentrated the tars which are recovered typically contain up to about 4 percent by weight rhodium after the volatile constituents have been removed. It has been difficult to separate all the rhodium (or other noble metal) from such tars by extraction with acid solutions and other techniques suggested by the prior art. We have now found that it is possible to extract the tars directly from the carbonylation reaction mixture, or the concentrates which are obtained when the reaction mixture is flashed, by contacting with suitable solvents capable of selectively removing the tars and leaving the rhodium behind for further use.

The carbonylation reaction mixture typically produces high-boiling residues or tars which may be tolerated, but which cannot be allowed to accumulate indefinitely since they may reduce the reaction rate. The rate at which the tars are produced and their composition will depend upon many factors, not fully understood at this time. Generally, in the carbonylation of methyl acetate to acetic anhydride, it is expected that the tar make will be up to about 5 parts by weight of tar for each 1000 parts of acetic anhydride produced, but substantially greater production of tars may occur when abnormal conditions prevail in the reactor. Experience suggests that the tar make in the carbonylation of methyl acetate to EDA is lower, up to about 2 parts by weight of tar for each 1000 parts of EDA. The rate at which the tars should be removed and the level to which they are permitted to accumulate in tne reaction mixture is established empirically for a particular reaction system. Typically, the reactor will be operated so that the products and other light materials will be flashed off — either from the entire reacting mixture or from a slip stream which is recycled to the reactor. In either case, heavier materials not flashed off accumulate and a portion of these materials is separated and then concentrated to leave only the heaviest materials, designated as tars.

According to our invention the tars, i.e. the heaviest residues, are separated from the reaction mixture or concentrations thereof by a selective extraction with suitable solvents. It has been discovered that by proper selection of the solvents and the operating conditions that the tars can be removed and the noble metals (typically rhodium) remain with the lighter materials.

PRACTICAL APPLICATION OF TAR SEPARATION BY SOLVENT EXTRACTION

The solvent extraction of tarry residues will be generally considered with reference to a block diagram, FIG. 1. The reaction generally takes place in a pressure vessel 10 and the reactants such as esters, ethers, alcohols and the like are carbonylated in the presence of carbon monoxide with or without hydrogen being present, in the presence of a noble metal catalyst and organic and/or metallic promoters. The tars produced can be tolerated in a reaction vessel to only a limited extent since they may reduce the reaction rate and may reduce the volume available for the carbonylation reaction. It will be determined empirically for any reaction system, what level of tar can be tolerated. Typically, the tars must be purged in some manner in order to maintain the selected concentration. This could be done by either periodically or continually purging the reaction system. In either case, the purge stream containing tars would contain many other compounds as well as noble metal catalyst which must be removed before the tars can be disposed of. In the diagram, a stream of the reactor contents is withdrawn via line 12 and flashed to a lower pressure from which products and other light materials may be separated for recovery. In one mode carrying out the reaction, this stream 12 would represent a withdrawal of all the products of the reaction. The flash would produce a vapor stream containing all of the products and by-products. Alternatively, the stream 12 may represent a periodic or continual small purge from the reactor, if it is operated in such a manner that products are continually vaporized from the reactor itself via optional line 13. In such an operation, vapor would be withdrawn from via line 13 the reactor 10 and combined with the vaporized material in line 15 from the flashed purged stream.

It will be appreciated that the liquid remaining after such flashes will contain the heavy tarry residues as well as the noble metal catalyst and the promoters. Also, the liquid will contain a certain amount of valuable products and other light materials which should be recovered. This tar-containing material then is stream 16, which will be subjected to solvent extraction according to the invention in order to separate the tars from the catalyst and promoters and insofar as possible from the reaction products and by-products.

As will be seen, a large number of solvents may be used, although practical considerations will govern the actual selection of the solvent. The desired characteristics of solvent(s) which are selected include the following:

1. The solvent must remove proportionately a larger fraction of the tars than of the noble metal catalyst present in the purged stream. This characteristic is critical to the selective separation of the tar and the noble metal.

2. The solvent should take up all species of tar compounds which may be present. A selective build up of particular types of tars should be avoided if possible.

3. The solvent should remove a minimum of the reactor products and by products.

4. Physical separation of the tar-containing solvent phase from the remainder of the mixture should be easily done. That is, the solvent and the flashed liquid should be substantially immiscible.

5. The solvent should be easily separated from the residual reaction products and by-products which are extracted along with the tars This characteristic is important to minimize the recirculation and build up of these reaction compounds in the extraction system.

6. The solvent should be chemically un-reactive with respect to the carbonylation reactants and products.

As the block diagram shows, a selective solvent or solvents is contacted (18) with the tar-containing stream. Methods of carrying out such extractions are well known in general to those skilled in the art. Typical of the techniques which would be considered is mixing of the solvent and the tar-containing stream followed by settling and separation, in one or more stages. Continuous countercurrent extraction in tray or packed towers would also be considered as a potentially useful method. Other types of equipment or variations of those generally discussed would be studied by those skilled in the art to make a final selection of the equipment to be used.

It is assumed for purposes of the diagram that a separation is made into two distinct product streams, the first being a recycle stream (20), which contains any unextracted tars, reaction products and by-products, and noble metal catalyst and promoters, along with a limited amount of the solvent. Such a stream may be directly recycled into the reactor or it may be further treated prior to reuse in the reactor. Typically, sufficient solvent could be present in this stream so that separation of the solvent is required to avoid a build up of solvent in the reactor system or undesirable interactions witn reaction products or by-products.

The tar-containing solvent stream (22) will be sent to separation facilities (24) which typically would involve evaporation of the solvent and recycle to the extraction system via line 26. The concentrated tar stream 28 would be disposed of, typically by incineration.

It will be appreciated by those skilled in the art that this broad outline of the application of the invention necessarily includes many alternative routes to carrying out the process of the invention. The proper selection of the solvent or solvent mixture, the mode of carrying out the extraction and the extent to which the tar and catalyst are separated made would require careful analysis in a specific carbonylation system. For example, the extraction might be carried out in sequential extractions in which different solvents are used, if such was found to be desirable to optimize the separation for a particular application. Separation of the solvent from reactor products to avoid adverse effects on the carbonylation reaction may be important in some applications. Once those skilled in the art become aware of the selective extraction with a solvent or solvent mixture of the tars formed in carbonylation reactions preferentially leaving behind the noble metal catalyst, a number of alternative schemes will suggest themselves for consideration in applying the invention. Preferred processes are disclosed and claimed in commonly-assigned application Ser. No. 267,960 by R. Porcelli, which is incorporated by reference herein.

PREPARATION OF CARBOXYLIC ACID ANHYDRIDES

The process for the preparation of an anhydride of a monocarboyxlic acid in general comprises carbonylation of a carboxylate ester (RCOOR) or an ether (ROR) under substantially anhydrous conditions in the presence of a Group VIII noble metal catalyst and a halogen. The R's may be the same or different and each R is a monovalent hydrocarbon radical or a substituted monovalent hydrocarbon radical wherein any substituent is inert.

Of particular interest, acetic anhydride can be effectively prepared by carbonylating methyl acetate or dimethyl ether under a moderate CO partial pressure in the presence of a Group VIII noble metal catalyst and iodides or bromides. Other alkanoic anhydrides, such as propionic anhydride, butyric anhydrides and valeric anhydrides, can be produced by carbonylating the corresponding lower alkyl alkanoate or a lower alkyl ether.

PREPARATION OF ETHYLIDENE DIACETATE

The preparation of ethylidene diacetate comprises contacting (a) methyl acetate and/or dimethyl ether, (b) carbon monoxide, and (c) hydrogen with a source of halide comprising a bromide and/or an iodide, within a reaction zone under substantially anhydrous conditions in the presence of a Group VIII noble metal catalyst effective to promote the formation of ethylidene diacetate. Although the process could be carried out in the vapor phase, liquid phase operation is preferred and will be described.

The overall reaction can be expressed by the following chemical equation:

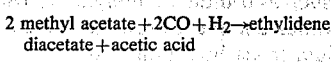
2 methyl acetate+2CO+H₂→ethylidene diacetate+acetic acid

When dimethyl ether is used as the reactant in lieu of methyl acetate, the overall reaction can be expressed by the following chemical equation:

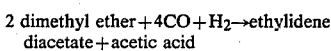
2 dimethyl ether+4CO+H₂→ethylidene diacetate+acetic acid

Co-products are often obtained such as acetic anhydride and/or acetaldehyde. The nature and distribution of these co-products depends in large measure upon the ratio of carbon monoxide to hydrogen employed, as well as other reaction variables.

When using dimethyl ether as the organic raw material it is believed that the initial step involved is the carbonylation of the ether to produce methyl acetate. This may be done in a separate reaction zone. However, the use of a separate reaction zone is not necessary because the conversion of dimethyl ether to methyl acetate can be carried out concurrently with and in the same reaction zone as that in which the ethylidene diacetate is formed. While hydrogen is a necessary co-reactant with carbon monoxide for the production of ethylidene diacetate, it is not a necessary co-reactant for the conversion of dimethyl ether to methyl acetate.

The molar ratios of carbon monoxide plus hydrogen to dimethyl ether and/or methyl acetate employed are dictated by the partial pressure criteria set forth below, since partial pressure and liquid phase concentration of these normally gaseous reactants are directly interrelated.

Once the reaction has been carried out, the reaction effluent is withdrawn from the reaction zone and distilled. Ethylidene diacetate and co-product acetic acid are recovered and unconverted or partially converted materials and halogen-containing components of the reaction medium are recovered for recycle to the reaction zone. The catalyst can also be readily recovered for recycle to the reaction zone.

REACTION CONDITIONS

In carrying out the reactions, a wide range of temperatures, e.g. 20° to 500° C., are suitable but temperatures of 100° to 300° C. are preferably employed and the more preferred temperatures generally lie in the range of 125° to 250° C. The reaction is carried out under superatmospheric pressure and employing a carbon monoxide partial pressure which is preferably 0.35 to 140.6 kg/cm$^2$, and most preferably 1.76 to 70.3 kg/cm$^2$, although carbon monoxide partial pressures of 0.007 to 1055 kg/cm$^2$ can also be employed. The partial pressure of hydrogen present, if any, will be consistent with the desired carbon monoxide pressure and the ratio of hydrogen to carbon monoxide as discussed hereinafter. The total pressure is preferably that required to maintain the liquid phase.

The Group VIII noble metal catalyst, i.e., iridium, osmium, platinum, palladium, rhodium and ruthenium, can be supplied in the zero valent state or in any higher valent form. For example, the catalyst to be added may be the metal itself in finely divided form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Similarly complexes of the metals can be employed for example the metal carbonyls, such as iridium carbonyls and rhodium carbonyls, or as other complexes such as the carbonyl halides, e.g., iridium tri-carbonyl chloride

or the acetylacetonates, e.g. rhodium acetylacetonate

Preformed ligand-like complexes can also be employed, such as dichloro bis-(triphenylphosphine) palladium, dichloro bis-(triphenylphosphine) rhodium, and trichloro tris-pyridene rhodium. Other forms in which the catalyst (as rhodium) can be added to the system include, aside from those already specifically listed, rhodium oxide (Rh$_2$O$_3$), tetrahodium dodecacarbonyl, dirhodium octacarbonyl, hexarhodium hexadecacarbonyl (Rh$_6$(CO)$_{16}$), rhodium (II) formate, rhodium (II) acetate, rhodium (II) propionate, rhodium (II) butyrate, rhodium (II valerate, rhodium (III) naphthenate, rhodium dicarbonyl acetylacetonate, rhodium trihydroxide, irdenylrhodium dicarbonyl, rhodium, dicarbonyl (1-phenylbutane-1,3-dione), tris(hexane-2,4-dione) rhodium (III), tris(heptane-2,4-dione) rhodium (III), tris(1-phenylbutane-1,3-dione) rhodium (III), tris(3-methylpentane-2,4-dione) rhodium (III), and tris(1-cyclohexylbutane-1,3-dione) rhodium (III).

The noble metal catalyst can be employed in forms initially or eventually soluble in the liquid phase reaction medium to provide a homogenous catalyst system. Alternatively, insoluble (or only partially soluble) forms, providing a heterogeneous catalyst system, can be employed. Amounts of carbonylation catalyst (calculated as contained noble metal based upon the total quantity of liquid phase reaction medium) of as little as about 1×10$^{-4}$ wt. % (1 ppm) are effective, although normally amounts of at least 10 ppm, desirably at least 25 ppm, and preferably at least 50 ppm would be employed. An optimum balancing of reaction rate and economic criteria would normally suggest the use of amounts of contained noble metal carbonylation catalyst based upon the total weight of liquid phase reaction medium between about 10 and about 50,000 ppm, desirably between about 100 and 25,000 ppm, and preferably between about 500 to 10,000 ppm.

Activity of the Group VIII noble metal catalysts described above can be significantly improved, particularly with respect to reaction rate and product concentration, by the concurrent use of a promoter. Effective promoters include the elements having atomic weights greater than 5 of Groups IA, IIA, IIIA, IVB, VIB, the non-noble metals of Groups VIII and the metals of the lanthanide and actinide groups of the Periodic Table. Preferred inorganic promoters include the metals of Groups VIB and the non-noble metals of Group VIII, especially chromium, iron, cobalt, and nickel and most preferably chromium. Particularly preferred are the lower atomic weight metals of each of these groups, i.e. those having atomic weights lower than 100, and especially preferred are the metals of Groups IA, IIA and IIIA. In general, the most suitable elements are lithium, magnesium, calcium, titanium, chromium, iron, nickel and aluminum. The promoters may be used in their elemental form e.g. as finely-divided or powdered metals, or they may be employed as compounds of various types, both organic and inorganic, which are effective to introduce the element into the reaction system, such as oxides, hydroxides, halides, e.g. bromides and iodides, oxyhalides, hydrides, alkoxides, and the like. Especially preferred organic compounds are the salts of organic monocarboxylic acids e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts e.g. salts of the mono-carboxylic acid corresponding to the anhydride being produced. Mixtures of promoters can be used, if desired, especially mixtures of elements from different Groups of the Periodic Table.

The quantity of the promoter can vary widely, but preferably it is used in the amount of 0.0001 mol to 100 mols per mol of Group VIII noble metal catalyst, most preferably 0.001 to 10 mols per mol of catalyst.

In the working up of the reaction mixtures, e.g. by distillation, as discussed above, the promoter generally remains with the Group VIII noble metal catalyst, i.e. as one of the least volatile components, and is suitably recycled or otherwise handled along with the catalyst.

Suitable organic promoters are non-hydrocarbon materials capable of forming a coordination compound with the Group VIII noble metal catalyst, containing within their molecular structure one or more pairs of electrons available for formation of coordinate bonds with the noble metal catalyst. Most such organic promoters can be characterized as Lewis bases for the particular anhydrous reaction system involved. Such promoters can be introduced concurrently with the reactants to the reaction zone or can be incorporated together with the Group VIII noble metal by formation of ligand complexes with the noble metal prior to introduction of the noble metal-ligand complex to the reaction zone.

Suitable organic promoters are organo-phosphine, organo-arsine, organo-stibine, organo-nitrogen, and organo-oxygen containing compounds. Organo-phosphine and organo-nitrogen promoters are preferred classes.

Suitable oxygen-containing compounds capable of functioning as organic promoters in this system are those containing functional groups such as the phenolic hydroxyl, carboxyl, carbonyloxy and carbonyl groups. Suitable organo-nitrogen containing compounds are those containing amino, imino and nitrilo groups. Materials containing both oxygen and nitrogen atoms can be used.

Illustrative organic promoters of the types mentioned above may be found in British Patent No. 1,538,782.

The quality of organic promoter employed is related to the quantity of noble metal catalyst within the reaction zone. Normally the quantity is such that at least 0.1, desirably at least 0.2, and preferably at least 0.3 mol of promoter compound per mol of noble metal is present in the reaction zone. Preferably less than 100 mols of promoter per mol of noble metal catalyst would be used.

It will be understood that metallic and organic promoters are not exclusive. Either, or both, may be included as is found to be preferred for particular applications.

Carbon monoxide and hydrogen preferably employed in substantially pure form, as available commercially. However, inert diluents such as carbon dioxide, nitrogen, methane, and/or inert gases (e.g., helium, argon, neon, etc.) can be present.

For the reactions of particular interest, all reactants should be substantially free from water since, in this fashion, the maintenance of a substantially anhydrous condition within the reaction zone is facilitated. (It may be noted that, generally speaking, the presence of water may be desirable in other carbonylation reactions where the products contain hydroxyl groups). The presence of minor amounts of water, however, such as may be found in these commercially available reactants, is permissible. Normally, however, the presence of more than 5 mol % of water in any one or more of the reactants should be avoided, tne presence of less than 3 mol % of water is desired, and the presence of less than 1.0 mol % of water is preferred. More important, however, than the amount of water in feed or recycle streams introduced to the reaction zone is the concentration of free water plus alcoholic hydroxyl groups (which react in situ to form water) present within the reaction zone. In practice, the molar ratio of (a) water plus the molar equivalents of alcoholic hydroxyl groups to (b) the number of mols of dimethyl ether and/or methyl acetate within the reaction zone is the most convenient method for defining this concentration. On this basis, this ratio preferably should not exceed 0.1:1. Still lower values for this ratio are advantageous, with optimal results being obtained with values for this ratio ranging from zero to 0.05:1.

Solvents or diluents can be employed, preferably materials which are indigenous to the reaction system and/or co-products commonly found in the reaction system. Excess dimethyl ether and/or methyl acetate are the preferred reaction diluents, with acetic acid being the preferred alternates. It is also practicable to employ organic solvents or diluents which are inert in the environment of the process. The most suitable inert solvents or diluents are hydrocarbons free from olefinic unsaturation, typically the paraffinic cycloparaffinic, and aromatic hydrocarbons such as octane, benzene, toluene, the xylenes and cyclododecane. Other suitable solvents include chloroform, carbon tetrachloride, and acetone.

The reaction to form carboxylic anhydrides requires the presence of a halide, which would be a component of the liquid phase reaction medium. Suitable halides are either bromide or iodide or mixtures thereof, iodide being preferred. The halide would usually be present largely in the form of methyl halide, acetyl halide, hydrogen halide, or mixtures of the foregoing species, and could be introduced to the liquid phase reaction medium as such. However, these materials may be formed in situ, by using inorganic halide materials, e.g., salts such as the alkali metal and alkaline earth metal salts, as well as elemental iodine and bromine. In continuous operation, wherein reaction by-products are separated and recycled to the reaction medium, organic halides such as methyl halide will be present as components of the liquid phase reaction medium and can be recovered and recycled to the reaction zone as such; thus, only a small quantity of make-up halide need be supplied to compensate for such losses in recovery as may be encountered.

The amount of halide that should be present in the liquid phase reaction medium is related to the amount of ether and/or ester reactant introduced to the reaction zone, but otherwise can vary over a wide range. Typically, 0.5 to 1,000 mols of ester and/or ether per equivalent of halide, desirably 1 to 300 mols per equivalent, and preferably 2 to 100 mols per equivalent are used. In general, higher proportions of halide to ether and/or ester reactant tend to increase reaction rate.

It has been found that molar ratios of carbon monoxide to hydrogen, broadly within the range of 1:100 to 100:1, desirably within the range of 50:1 to 1:50, and preferably within the range of 10:1 to 1:10 can be employed. Best results are obtained with carbon monoxide-hydrogen mixtures which approach the stoichiometric ratios of carbon monoxide to hydrogen. Molar ratios of carbon monoxide to hydrogen within the range of 0.5:1 to 5:1 are thus an especially preferred regime of operation.

The following example will illustrate a carbonylation process which produces heavy residues containing substantial amounts of rhodium.

EXAMPLE 1

A four liter autoclave was operated continuously to produce acetic anhydride by the carbonylation of methyl acetate. The reactants, i.e. methyl acetate, methyl iodide, carbon monoxide and hydrogen are added continuously. The product acetic anhydride is obtained as a vapor by flashing a withdrawn stream of the reacting mixture. The remaining liquid is recycled to the reactor. The reaction is catalyzed by the mixture of rhodium trichloride trihydrate, and lithium iodide, which are added to the inital charge placed in the autoclave in amounts sufficient to provide about 0.01 mol Rh/liter of liquid in the vessel and 50 mol Li/mol Rh. The reaction is operated at about 180° C., 54.8 kg/cm$^2$ absolute, with partial pressures of about 35 kg/cm$^2$ CO and about 5.6 kg/cm$^2$ H$_2$. The liquid recycled after flashing contains about 4 wt. % methyl iodide, 7 wt. % methyl acetate, 32 wt. % acetic anhydride, 24 wt. % acetic acid, with about 1-2 wt. % heavy residues. A slipstream is withdrawn from the recycle stream at a rate sufficient to maintain the residues in the autoclave at an acceptable level. The tar-containing liquid which remains after the gases have been separated is treated with solvents to remove the tar content while excluding the rhodium.

EXAMPLE 2

The tar-containing liquid from Example 1 includes about 1-2 wt. % tars, along with a mixture of the reactants and products. The tar portion is separated for testing by contacting a 16 gm sample with about 25 mls of methanol and refluxing at atmospheric pressure for about one hour, then removing the volatile portion of the mixture at 50° C. and a vacuum below 10 mm Hg. The resulting viscous material is dissolved in 10 ml of acetone. A 5 ml aliquot of the resulting solution is added to a 500 ml separating funnel and dried with nitrogen. Then, 20 ml of methylene chloride and 40 ml of aqueous 10% HCl are added to the separatory funnel and vigorously shaken. Two phases separated. The aqueous upper layer contains the soluble rhodium and is retained. The lower organic layer contains the tar and is drained into a second 500 ml separatory funnel containing 40 ml of aqueous 10% HCl. The extraction is repeated and the lower layer drained into an 8 oz glass bottle. A fresh 20 ml portion of methylene chloride is added to the first separatory funnel and the procedure repeated with the methylene chloride being drained into the 8 oz bottle.

For solvent testing, 4 ml aliquots of the tar-containing methylene chloride are added to 6 dram vials and the methylene chloride evaporated by heating to 35°-40° C. in the presence of a stream of nitrogen. A 1 ml aliquot of the solvent to be tested is added to the vial and shaken. Thereafter, the vial is centrifuged to remove suspended solids. The liquid portion is analyzed for tar by gel permeation chromatography using a two column bank, refractive index detector, and computerized area integration. The columns were 500 Å µ Styragel and 100 Å µ Styragel supplied by Waters Associates, Milford, Mass. The mobile phase was methylene chloride. The amount of rhodium extracted was measured by atomic absorption spectroscopy. The results of a series of tests with various solvents are given in the following table.

TABLE I

| Solvent | % Rh Extracted | % Tar Extracted |
|---|---|---|
| hexane | 2.2 | 20 |
| cyclohexane | 5.8 | 23 |
| methylene chloride | 54 | 100 |
| carbon tetrachloride | 1.7 | 19 |
| toluene | 6.3 | 45 |
| ethyl ether | 22 | 83 |
| isopropanol | 57 | (a) |
| ethanol | 77 | (a) |
| ethyl acetate | 68 | 100 |
| acetonitrile | 81 | 84 |

(a) values above 100 measured due to solvent interference - visual appearance indicated that substantially all of the tar solids were dissolved.

Preferred solvents would be those which extract very little rhodium, but significant amounts of the tars. Of those tested, hexane, cyclohexane, carbon tetrachloride, and toluene would be representative of classes of solvents which are most likely to be successfully used to extract tars. The remaining solvents appear to extract more rhodium than desirable, but they might still be useful if extraction of a larger amount of tar was desired and if the rhodium is recovered from the solvent.

EXAMPLE 3

In Example 2, batch extraction of tar is from an immobile residue remaining after removal of volatiles, lithium, and part of the rhodium and iodine by aqueous HCl. However, a liquid-liquid extraction can be performed directly from the flashed reaction liquid. For such an extraction a solvent must be able to form a second phase when contacted with the tar containing liquid, and have reasonable tar solubility and minimal catalyst solubility. One suitable solvent is cyclohexane.

Cyclohexane is tested in various volume ratios of solvent to flashed reaction liquid of Example 1. The tar content in the reaction liquid is about 4.5%. Cyclohexane is contacted with flashed reaction liquid in a closed vessel. The mixture is shaken for 10-15 minutes, then centrifuged to remove any suspended material. An aliquot of the cyclohexane phase is removed and dried to constant weight at 50° C. and <10 mm Hg vacuum. The residue was analyzed for rhodium and lithium by atomic absorption spectroscopy. The total amount of tar and catalyst extracted was calculated. The results are listed in Table II.

TABLE II

| Volume of Cyclohexane (ml) | Volume of Flashed Reaction Liquid (ml) | % Rhodium Extracted | % Lithium Extracted | % Tar Extracted |
|---|---|---|---|---|
| 5 | 10 | 0.03 | 0.14 | 22 |
| 5 | 10 | — | — | 22 |
| 10 | 10 | 0.04 | 0.19 | 30 |
| 10 | 10 | — | — | 24 |
| 20 | 10 | 0.05 | 0.29 | 26 |
| 20 | 10 | — | — | 26 |
| 20 | 5 | 0.06 | 0.41 | 29 |
| 20 | 2 | 0.06 | 0.07 | 36 |
| 20 | 2 | — | — | 34 |

EXAMPLE 4

In contrast to Examples 2 and 3, which were batch extractions, a continuous countercurrent extraction is carried out on a flashed reaction liquid, containing acetic anhydride, reactants, and by-products where the tar content is determined to be about 2.5 wt. percent. A second continuous extraction is carried out on a sample of unflashed reaction liquid, in which the tar content is about 1.9 wt. percent. The heavies-containing liquids are fed into the top of a cylindrical extraction column 2.5 cm id. and 64 cm long and having three 2.4 cm impellers 10 cm apart on a central shaft driven by a motor at 600 rpm. Cyclohexane is fed into the bottom of the column and passes upward countercurrently to the heavies-containing liquid. Analysis of the two phases after contacting shows the following results.

TABLE III

| Test | Cyclohexane Rate, cc/hr | Tar-Containing Liquid, cc/hr | Removed by cyclohexane as percent in feed | |
|---|---|---|---|---|
| | | | Rh | Tar |
| 1 | 100 | 100 | 0.09 | 29.3 |
| 2 | 90 | 60 | 0.06 | 20 |

The results of Table III show that cyclohexane can remove substantial amounts of the tars contained in the liquid feed while leaving the rhodium behind. It should be be noted that the tars need not be completely removed since in a practical application only sufficient tars to correspond to the amounts being produced must be removed to maintain a constant level in the reacting mixture. Further, the relative amount of solvent used and the conditions of the extraction would be adjusted to optimize the removal of tars while minimizing the loss of rhodium to nearly zero.

The results presented illustrate that tar and rhodium can be separated by choice of a proper solvent. Batch extraction of tar residue remaining after aqeuous acid extraction of lithium and some rhodium was shown to be successful to varying degrees depending on solvent chosen. Suitable solvents include alkanes, cycloalkanes, halogenated alkanes, and aromatic hydrocarbons. More generally, the solvents may be characterized as belonging to selectivity groups I, VIb, and VII as defined by Snyder, *Journal of Chromatography,* 92, 233–230, 1974, and incorporated herein by reference plus the alkanes and cycloalkanes which are not assigned to a group by Snyder. Snyder classifies solvents according to the following table on page 229.

| Group | Solvents |
| --- | --- |
| I | Aliphatic ethers, trialkyl amines, tetramethylguanidine |
| II | Aliphatic alcohols |
| III | Pyridines, tetrahydrofuran, amides (except the more acidic formamide) |
| IV | Glycols, glycol ethers, benzyl alcohol, formamide, acetic acid |
| V | Methylene chloride, ethylene chloride, tricresyl phosphate |
| VIa | Alkyl halides, ketones, esters, nitriles, sulfoxides, sulfones, aniline and dioxane |
| VIb | Nitro compounds, propylene carbonate, phenyl alkyl ethers, aromatic hydrocarbons |
| VII | Halobenzenes, diphenyl ether |
| VIII | Fluoroalkanols, m-cresol, chloroform, water |

Liquid-liquid extraction of tar directly from reactor effluents requires solvent immiscibility with the effluent. Solvents best suited are alkanes or cycloalkanes. In addition, alkanes or cycloalkanes doped with a stronger tar removing solvent and still producing a second phase may extract more tar.

What is claimed is:

1. A process for the selective removal of high molecular weight rhodium-containing tars containing organic carbonyl and acetate function produced in rhodium-lithium catalyzed carbonylation reactions in which methyl acetate or dimethyl ether are combined with carbon monoxide in the presence of iodides to form acetic anhydride or ethylidene diacetate comprising extracting said tars from carbonylation reaction mixtures or concentrates thereof with a liquid solvent substantially immiscible with said mixtures and concentrates and capable of preferentially dissolving said tars relative to the contained rhodium while removing a minimum of carbonylation products and by-products and comprising at least one member of the group consisting of alkanes, cycloalkanes, and solvents belonging to Groups I, VIb, and VII as defined by Snyder, *J. of Chromatography,* 92, p. 223–230, 1974 and thereafter separating the tar-containing solvent from said mixtures and concentrates, recovering said solvent, discarding said tar, and recycling said separated mixtures or concentrates to said carbonylation reaction.

2. The process of claim 1 wherein said solvent is separated from said tars and reused.

3. The process of claim 1 wherein said solvent is contacted with the tar-containing liquid concentrate resulting from the flashing of a carbonylation reaction mixture from reaction pressure to a lower pressure to remove a portion of low-boiling reactants and reaction products.

4. The process of claim 3 wherein said solvent is contacted with a substantially solid tar concentrate resulting from the removal of volatile compounds from said tar-containing liquid concentrate.

5. The process of claim 1 wherein said solvent is at least one member of the group consisting of alkanes, cycloalkanes, halogenated alkanes, and aromatic hydrocarbons.

6. The process of claim 5 wherein said solvent is cyclohexane.

7. The process of claim 5 wherein said solvent is toluene.

8. The process of claim 5 wherein said solvent is carbon tetrachloride.

9. The process of claim 1 wherein the volume ratio of said solvent to said tar is between about 0.5 and 10.

* * * * *